(12) United States Patent
Beck et al.

(10) Patent No.: US 10,792,028 B2
(45) Date of Patent: Oct. 6, 2020

(54) DOUBLE RETRACTOR BLADES

(71) Applicant: AESCULAP AG, Tuttlingen (DE)

(72) Inventors: Thomas Beck, Durchhausen (DE);
Pedro Morales, Tuttlingen (DE);
Christian Huber, Mülheim (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 14/383,633

(22) PCT Filed: Mar. 7, 2013

(86) PCT No.: PCT/EP2013/054668
§ 371 (c)(1),
(2) Date: Sep. 8, 2014

(87) PCT Pub. No.: WO2013/132039
PCT Pub. Date: Sep. 12, 2013

(65) Prior Publication Data
US 2015/0099939 A1 Apr. 9, 2015

(30) Foreign Application Priority Data

Mar. 9, 2012 (DE) .......................... 10 2012 004 555

(51) Int. Cl.
*A61B 17/02* (2006.01)
*A61B 90/00* (2016.01)

(52) U.S. Cl.
CPC .......... *A61B 17/0293* (2013.01); *A61B 17/02* (2013.01); *A61B 2017/0237* (2013.01); *A61B 2090/0813* (2016.02)

(58) Field of Classification Search
CPC .......................... A61B 17/02; A61B 2017/0237
(Continued)

(56) References Cited

U.S. PATENT DOCUMENTS 2,002,021 A * 5/1935 Rouse ................ A61B 17/6408
606/105
2,670,731 A * 3/1954 Zoll .................... A61B 17/0206
600/232

(Continued)

FOREIGN PATENT DOCUMENTS

DE 35 09 787 A1 10/1985
DE 29806973 U1 * 8/1998
(Continued)

OTHER PUBLICATIONS

English Machine Translation of EP0951868, accessed Nov. 30, 2019.*
(Continued)

*Primary Examiner* — Jan Christopher L Merene

(57) ABSTRACT

The present application relates to a double blade for a surgical retractor having a base body with a substantially cylindrical mounting mandrel for mounting the double blade on a surgical retractor, and at least two blade elements that are so mounted on the base body as to be rotatable and/or displaceable through at least a certain angular range with respect to the base body. Moreover, the present application relates to a blade arrangement in which a double blade is connected to a connecting element of a further double blade, or a single blade. In this case, the at least one double blade or, optionally, the single blade is rotatable with respect to the connecting element. In addition, the application relates to a retractor with a double blade, a blade arrangement or a blade assembly comprising double blades and a blade arrangement.

20 Claims, 2 Drawing Sheets

(58) Field of Classification Search
USPC .......................................................... 600/214
See application file for complete search history.

(56) References Cited

U.S. PATENT DOCUMENTS

| | | | | |
|---|---|---|---|---|
| 3,750,652 A * | 8/1973 | Sherwin | ............... | A61B 17/025 606/90 |
| 4,616,635 A | 10/1986 | Caspar et al. | | |
| 5,052,373 A * | 10/1991 | Michelson | ......... | A61B 17/0206 600/217 |
| 5,067,477 A * | 11/1991 | Santangelo | ........ | A61B 17/0206 600/222 |
| 5,339,801 A * | 8/1994 | Poloyko | ............. | A61B 17/0218 600/214 |
| 5,365,921 A * | 11/1994 | Bookwalter | ....... | A61B 17/0206 269/261 |
| 5,722,935 A * | 3/1998 | Christian | ........... | A61B 17/0281 600/204 |
| 5,776,054 A * | 7/1998 | Bobra | ................ | A61B 17/0206 600/210 |
| 6,074,343 A * | 6/2000 | Nathanson | ......... | A61B 17/0206 600/214 |
| 6,808,493 B1 * | 10/2004 | Bookwalter | ........... | A61B 17/02 600/231 |
| 6,837,851 B1 * | 1/2005 | Valentini | ............ | A61B 17/0206 600/210 |
| 7,097,647 B2 * | 8/2006 | Segler | .................. | A61B 17/025 606/90 |
| 7,481,766 B2 * | 1/2009 | Lee | ........................ | A61B 17/02 600/214 |
| 8,007,435 B2 * | 8/2011 | Hartnick | ............ | A61B 17/0206 128/200.26 |
| 2002/0099269 A1 * | 7/2002 | Martin | ............... | A61B 17/0206 600/201 |
| 2004/0147935 A1 * | 7/2004 | Segler | ................. | A61B 17/8866 606/90 |
| 2008/0073922 A1 * | 3/2008 | Holtz | .................. | B25J 15/0213 294/198 |
| 2008/0077171 A1 * | 3/2008 | Blain | ................. | A61B 17/0206 606/190 |
| 2010/0286485 A1 | 11/2010 | Valentini et al. | | |
| 2011/0130793 A1 * | 6/2011 | Woolley | ............. | A61B 17/0206 606/279 |
| 2011/0144450 A1 | 6/2011 | Paolitto et al. | | |
| 2011/0172494 A1 | 7/2011 | Bass et al. | | |
| 2012/0296171 A1 * | 11/2012 | Lovell | ................ | A61B 17/0206 600/213 |
| 2012/0316400 A1 * | 12/2012 | Vijayanagar | ....... | A61B 17/0293 600/233 |
| 2012/0330106 A1 * | 12/2012 | Wright | ............... | A61B 17/0206 600/218 |
| 2013/0190575 A1 * | 7/2013 | Mast | .................. | A61B 17/7079 600/215 |

FOREIGN PATENT DOCUMENTS

| | | | |
|---|---|---|---|
| DE | 10 2006 036 117 A1 | 2/2008 | |
| EP | 0951868 A1 * | 10/1999 | ......... A61B 17/0206 |

OTHER PUBLICATIONS

International Search Report for PCT/EP2013/054668 dated Jun. 18, 2013.

* cited by examiner

DOUBLE RETRACTOR BLADES

DESCRIPTION

The present invention relates to a double blade, a blade arrangement and a blade assembly for a surgical retractor as well as a surgical retractor with a double valve, a valve arrangement and/or a valve assembly.

In cardiac surgery, the entire sternum is usually opened in order to be able to operate on or in the heart. Major trauma and a long recovery time may arise for the patient due to this surgical method. This often causes problems with infection and in healing. For this reason, doctors have developed new minimally invasive surgical techniques. An example of such a minimally invasive surgical technique is the so-called MIDCAB surgery (Minimally Invasive Direct Coronary Artery Bypass). In this operation, access to the operating area is not made through the sternum but laterally through the ribs of the patient. The ribs of the patient must be spread open for this, on the one hand to provide the surgeon with access to the operating area and, on the other hand, to allow him to look at or in the operating area. A surgical retractor with corresponding blades or blade elements is required to spread open the ribs.

PRIOR ART

Ordinary blades, such as those used in sternum surgery, are unsuitable for bending out the ribs because the shape of the blades is flat and straight. The anatomical characteristics of the ribs in the region of the lateral thorax are however different from those in the area of the sternum. The sternum is usually opened by as straight a section as possible. This is because the contact surfaces at the sternum are generally planar surfaces and a retractor for sternum surgery has blades that are suitable for engagement with substantially planar contact surfaces. On the other hand, the ribs of a patient are bent in a side view. If access to the operating area is effected between two adjacent ribs, the upper rib presents a convex contact surface while the lower rib presents a concave contact surface for the blades of the surgical retractor. Using a retractor with the conventional blade in the field of sternum surgery leads to the entire spreading force of the retractor being applied to the lower rib at only two points, namely the two side edges of the blade, but at only a single point in the case of the upper rib, i.e. about in the middle of the blade. This concentrated application of the spreading force of the retractor on the ribs of the patient may lead to accidental rib fractures or bone collapse or bone splitting. The present invention is intended to avoid these rib fractures and thus further reduce the recovery time of the patient.

A wide variety of surgical retractors are known in the prior art. In the document US 2011/0172494 is shown a surgical retractor, which enables lateral access to the chest cavity of the patient. This surgical retractor includes two curved blades, specifically a concave blade on one side and a convex blade on the opposite side. Due to the curvature or bending of the two blades of the retractor, how the retractor is to be used on patients may thus be determined directly. The concave blade must be applied to the convex upper rib while the convex blade must be applied to the concave lower rib. However, since the degree of bending or curvature of the blades is not particularly noticeable, there is a danger of confusion between the two blade curvatures.

SUMMARY

The object of the present invention is to create a means to produce lateral access to the chest cavity of a patient where a mix-up of the blades is of no consequence.

The task of the present invention is achieved by a double blade according to claim 1, a blade arrangement according to claim 12, a blade assembly according to claim 13 and a surgical retractor according to claim 15; further advantageous developments are the subject of the dependent claims.

According to a first aspect of the present invention, a double blade for a surgical retractor is disclosed with a base body having a substantially cylindrical mounting mandrel for assembly of the double blade to a surgical retractor, and at least two blade elements that are so mounted on the base body that they are rotatable and/or movable at least over a certain angular range with respect to the base body.

In this case, the blade elements may be displaced against a spring force.

In particular, they may then, if more than two blade elements are provided on one base body, be so displaceable with respect to one another that they may adapt to an arcuate rib, i.e. assume a concave or convex configuration. When the double blade is mounted on a retractor and the retractor is used on the patient by being inserted between two ribs of the patient, this displacement is in a cranial-caudal or upwards-downwards direction. If the blade elements of a double blade are arranged substantially next to one another, the said direction corresponds to a forwards-rearwards direction with respect to the double blade, whereby forwards describes the direction toward the incision. In this respect, it is particularly advantageous when the blade elements are displaceable forwards from a base position against a spring force.

If only two blade elements are provided, then these automatically adapt to the shape of each rib through their rotation. In the case of a concave rib, i.e. the lower rib, the two blade elements rotate towards one another slightly, while in the case of a convex rib, i.e. the upper rib, they rotate slightly away from one another. If more than two blade elements are provided on a base body, then in the case of a convex rib at least the central blade element or the central blade elements must be movable in the forwards-rearwards direction, so that all the blade elements may adapt to the shape of the rib by rotation in this case as well. In the case of a concave rib, all the blade elements must be movable in the forwards-rearwards direction except for the one central or the two central blade elements in order to allow such an adaptation. Advantageously, all the blade elements are then movably mounted on the base body. A complete rotation of the blade elements by 360° is not required, but may be implemented. It is crucial that the angular range is sufficiently large to allow adaptation to the convexity and concavity of the various ribs of different patients. However, the angular range need not be too large for this purpose.

The mounting mandrel is designed so that it may be received in a corresponding seat in a retractor arm and may be secured there to prevent it dropping out. A similar mounting may also be provided on a connecting element.

According to an advantageous further development of the first aspect of the present invention, the mounting mandrel is configured so that when the double blade is mounted on a surgical retractor, then the base body of the double blade is rotatable at least through a predetermined angular range with respect to the surgical retractor.

With the rotation of the base body with respect to the surgical retractor, the positioning of the entire double blade with its at least two blade elements adapts to the geometric characteristics of the point of application, so that no torque is transmitted to the arm of the retractor and no torque is transmitted from the arm of the retractor to the double blade, where torque could lead to an excessive impact of a blade element on the point of application. Such an excessive impact could otherwise lead to unnecessary local traumas at the point of application.

According to a further advantageous development of the first aspect of the present invention, the mounting mandrel comprises an at least partially circumferential mounting groove.

Using the at least partially circumferential mounting groove, a positive connection between the double blade and an arm of the retractor may be effected without dispensing with rotation of the double blade or the base body with respect to the retractor. At least a spring-loaded ball, for example, may engage in the mounting groove to provide a positive-fit undercut. In addition, the positive fit may be secured against accidental release and thus unintentional release of the double blade from the retractor by means of a snap ring or the like, as is commonly practiced in pressure lines.

According to a further advantageous development of the first aspect of the present invention, the depth of the mounting groove is variable along its direction of rotation.

This, coupled with an undercut with a single spring-loaded ball, ensures that the double blade so aligns that the spring which pushes the ball into the mounting groove is maximally relaxed. This means that the base body of a load-free double blade returns to a position in which the ball abuts against the deepest point of the groove. To this end, the depth of the groove must vary continuously or steadily and must not have any local deep points. Usefully, this position, to which the base body of the double blade returns, is the base position of the double blade at which the connecting line of the fixing points of the blade elements to the base body is substantially parallel to the contact surface of the body cavity of the patient. Typically, this connecting line is also perpendicular to the distance control element of the retractor at the base position.

According to yet another advantageous further development of the first aspect of the present invention, the blade elements each have a proximal end through which they are received in the base body to which they are rotatably and/or displaceably fixed, and a free distal end.

When the proximal ends of the blade elements are received in recesses formed in the base body, the side walls of the said recesses can limit the rotation of the blade elements with respect to the base body. This is useful since a rotation of the blade elements through 360° is not useful in practice because the blade elements may adopt an incorrect position in the patient's body cavity to be spread open on insertion of the retractor, and may thus interfere with the insertion of the retractor. The blade elements may be received in a common recess, so that there is only one outer sidewall to limit outwards rotation of the respective blade element. However, the proximal ends of the blade elements do not need to be received in the base body, but may alternatively be attached to the top or the bottom of the base body.

According to a further advantageous development of the first aspect of the present invention, the base body has cleaning openings in the area in which the proximal ends of the blade elements are received in order to enable proper cleaning and sterilization of the double blade.

When using the double blade, blood, tissues, bone fragments or other debris may penetrate the openings in which the blade elements are received. This debris is very difficult to remove again if these openings are formed as blind holes. The cleaning openings make it possible to introduce a flushing fluid, such as compressed air, water, an aqueous soap solution or other cleaning liquid, through the cleaning openings, optionally under pressure, and thus flush out coarse and fine debris. This facilitates the cleaning process considerably. Advantageously, the cleaning openings are formed on the bottom surfaces of the blind holes, but they may also be provided at the top, the bottom or the side surfaces of the base body. What is important is that a connection is provided between the respective blind hole (i.e. the opening in which the at least one blade element is received) and the exterior of the base body. There may also be at least one cleaning opening that connects the various blind holes with one another.

According to a further advantageous development of the first aspect of the present invention, at least one blade element has a convexly curved inner surface that is lateral to the longitudinal axis of the blade element.

In the case of a convexly curved inner surface of a blade element or blade elements, the double blade may be displaced along the contact surface during insertion into the body opening of the patient without a lateral edge of the blade element wedging against the contact surface and, on further displacement of the double blade, twisting along the contact surface in such a way that it bears against the contact surface with a lateral surface, which may lead to increased trauma or even bone fractures at the contact surface.

According to a further advantageous development of the first aspect of the present invention, at least one blade element has a free end curved towards the inner surface of the blade.

This free end curved towards the inner side ensures an optimal fit of the double blade or blade elements against the bones to be bent outwards at the contact surface and prevents the double blade from slipping off the bones. In this case, the bone to be bent outwards is exactly at the inner surface of the bend of the free distal end of the blade elements.

According to a further advantageous development of the first aspect of the present invention, an elastic element is provided between at least one blade element and the base body, which presses the at least one blade element into a predefined basic position.

On insertion of a retractor with a double blade according to the invention, this arrangement prevents the rear side, i.e. the outer surface, of a blade element from abutting against the contact surface. Otherwise, this would hinder and slow down the insertion process. The elastic element need not be particularly strongly resilient.

According to a further advantageous development of the first aspect of the present invention, at least one blade element has a soft coating or padding on its inner surface.

Such a soft coating or padding distributes the pressure that is applied by the individual blade elements to the corresponding positions on the contact surface, thus reducing trauma occurring at the contact surface. This results in fewer overall trauma, less pain development in patients after surgery, and a faster and better healing of the wound.

According to a further advantageous development of the first aspect of the present invention, the rotation of at least one blade element with respect to the base body is limited.

For this purpose, a kind of stop is provided against which the blade element abuts after completing rotation through a certain angle. This stop may be provided in the area of the rotatable mounting of the blade element on the base body. Alternatively, a side surface of a blade element may abut such a stop. This is advantageous as rotation of the blade elements only offers advantages through a certain relatively small angular range, while an excessive rotation of the blade elements with respect to the base body might hinder insertion of the retractor.

According to a further advantageous development of the first aspect of the present invention, the longitudinal axis of each blade element is inclined at an angle α between 50° and 90°, preferably between 60° and 80°, and especially between 65° and 75° with respect to the plane of the base body.

The contact surface is not constituted exclusively of bone material. The bone material forms the innermost area of the contact surface. The distal end of the blade elements abuts there. There is a more or less thick layer of soft tissue above the bone material. The thickness of the soft tissue layer depends on the physical condition of the patient and of the place of surgery on the patient. If the angle α is 90°, the soft tissue is pushed exactly as far as the bones are bent outwards. At a smaller angle, the soft tissue will be pushed further outwards than the bones are bent. This leads to a sort of funnel in the area of the wound opening. The view of the surgeon inside the patient is enhanced because of the funnel. In the case of a small angle α under 50°, there is a risk of the blade elements slipping off the bone, which must be prevented at all costs, especially during surgery. An advantageous angle range is between 60° and 80°, as this guarantees a firm seating of the retractor in the body opening to be spread apart while providing a clear view for the surgeon. In the range of 65° and 75°, the seating of the blade elements on the bone is even better, while the view for the surgeon is very good as before.

According to a second aspect of the present invention, a blade arrangement for a surgical retractor is disclosed having a connecting element featuring a substantially cylindrical mounting mandrel and two mounting seats. A double blade according to any one of the preceding claims is mounted on a mounting seat of the connecting element. Either a further double blade or a single blade is mounted on the other mounting seat of the connecting element.

In the case of this second aspect, the mode of operation of the above double blade may be used for larger body openings. In this way, the mounting mandrel corresponds to the mandrel of the base component of the double blade, while the mounting seats correspond to the mounting seats on the retractor arm. Connecting elements may be formed in various lengths, while the blade arrangement may be assembled as required.

According to a third aspect of the present invention, a blade assembly is disclosed which comprises at least one connecting element having a substantially cylindrical mounting mandrel and two mounting seats. Either a further connecting element, a blade arrangement according to the second aspect of the invention, a double blade according to the first aspect of the invention or a single blade, is mounted on the two mounting seats of each connecting element.

The mode of operation of the second aspect of the present invention may be used more extensively with this structure. The force applied by the retractor on the contact surface may be distributed across a plurality of load application points. By means of an appropriate design of the blade assembly, a uniform load may be distributed to all blade elements. To this end, the lever arms and the number of blade elements on the levers should be in a constant relationship. The fewer the number of blade elements located on one side of the lever, the longer the lever arm must be in order to achieve a uniform force distribution via all the blade elements.

According to a fourth aspect of the present invention, a double blade, a blade arrangement or a blade assembly according to one of the above aspects is disclosed, whereby the single blades and/or blade elements are so bent at their free ends towards the inside of the single blades or blade elements, that the distal bending points lie on a straight line or an arc.

With such an arrangement, it may be ensured that all the blade elements lie firmly against the bones to be spread open, while not too much force is applied to the individual force application points. If the bending points lie on a straight line, the apparatus is suitable for a substantially straight body opening, for example for a sternum. If the bending points lie on an arc, this arc should be adapted to the bending of the bones to be spread open. Such a device is suitable, for example, for the lateral rib area.

According to a fifth aspect of the present invention, a surgical retractor with a double blade according to the first aspect of the invention and/or a blade arrangement according to the second aspect of the invention, or a blade assembly according to the third aspect of the invention is disclosed.

Further advantages and features of the invention are evident to persons skilled in the art from the accompanying drawings and the detailed description of the embodiments.

Figure 1:
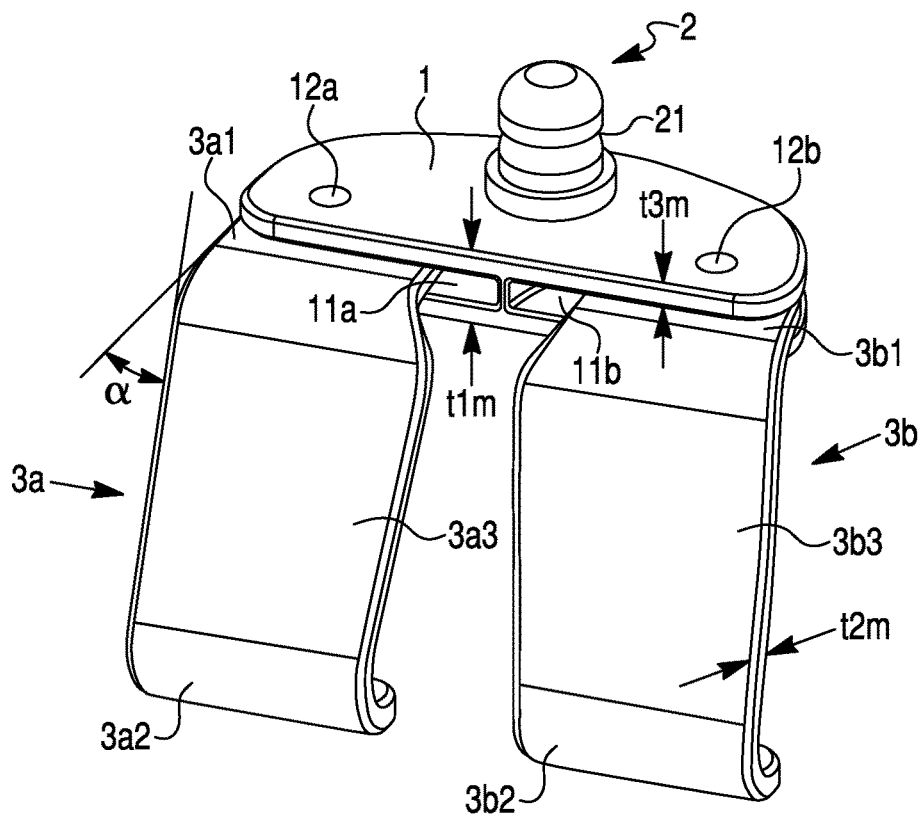
FIG. 1 shows a first embodiment of the present invention in a perspective view.

A first embodiment of the present invention is described in detail with reference to FIGS. 1 and 2. This embodiment relates to a double blade for a retractor, which is used to spread the ribs of a patient in the lateral area.

In the case of the first embodiment of the present invention, the double blade for a surgical retractor is configured with a base body 1 having a substantially cylindrical mounting mandrel 2 for mounting the double blade on a surgical retractor. The mounting mandrel 2 extends upwards from the surface of the base body 1. Moreover, the double blade has two blade elements 3a, 3b. The mounting mandrel 2 has a circular cylindrical shape with a circumferential mounting groove 21, which is located about halfway up the mounting mandrel 2. In this way, the mounting mandrel 2 has about the shape of a mushroom. In this embodiment, the circumferential mounting groove 21 has a constant depth.

The two blade elements 3a, 3b are received in two separate slots 11a, 11b in the base body 1 at their proximal ends 3a1, 3b1, and are each rotatably mounted on the base body 1 with the help of a pin 12a, 12b. The two slots 11a, 11b are formed in a side surface of the base body 1, which faces the body opening to be spread open when the double blade is in use. Both blade elements 3a, 3b have a flat inner surface 3a4, 3b4 in the lateral direction. The free distal end 3a2, 3b2 of each blade element 3a, 3b is bent over toward its inner surface 3a4, 3b4 to form, in this way, a sort of hook that engages with a rib of the patient and thus prevents the blade elements 3a, 3b from slipping off the rib. In the present case, no elastic element is provided to press the blade elements 3a, 3b into a basic position.

The rotation of each blade element 3a, 3b with respect to the base body 1 is limited in both directions. The web provided between the two slots 11a, 11b limits rotation of both blade elements 3a, 3b in the direction of the other blade element 3a, 3b, hereinafter referred to as an inwards rotation. As the two slots 11a, 11b each extend outwards via the rounded corner of the base body 1, the outwards rotatability is greater than the inwards rotatability. Nevertheless, the outer side walls of the two slots limit the outwards rotation of the respective blade element 3a, 3b. In fact, cleaning openings may be omitted due to the wide opening of the two slots 11a, 11b.

The proximal ends 3a1, 3b1 of the two blade elements 3a, 3b are parallel to the surface of the base body 1. In this embodiment, the central area 3a3, 3b3 of the two blade elements 3a, 3b is inclined downwards by 70° with respect to the proximal ends 3a1, 3b1. The bending of the distal ends 3a2, 3b2 towards the inner sides 3a4, 3b4 of the blade elements, i.e. away from the body opening to be spread open is so configured that the distal ends 3a2, 3b2 are approximately parallel to the proximal ends 3a1, 3b1. Accordingly, the deflection at the distal ends 3a2, 3b2 is about 110°.

Figure 2:
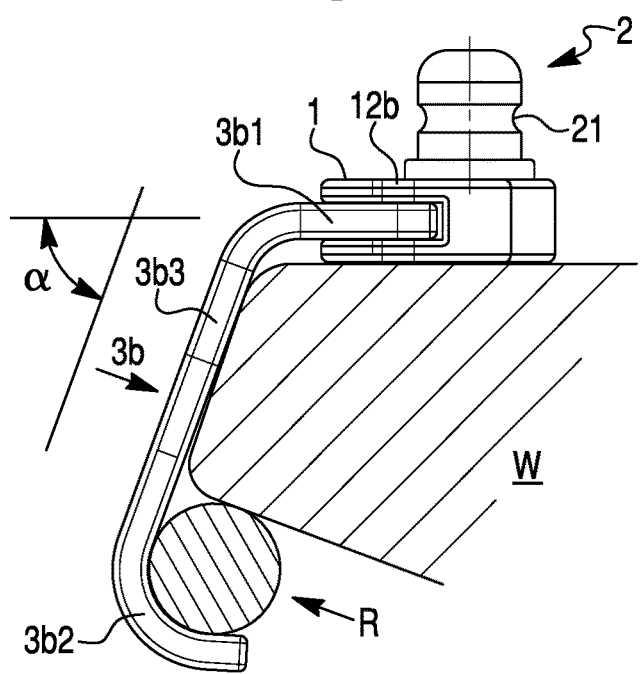
FIG. 2 shows a first embodiment of the present invention in a side view.

This 70° inclination of the central areas 3a3, 3b3 is with respect to the base body, as shown in FIG. 2, on the one hand to ensure a firm and reliable engagement with the rib R of the patient while, on the other hand, allowing a good view of the surgeon in the thus expanded body opening and accordingly the actual operating area. This is also achieved by the central areas 3a3, 3b3 of the blade elements 3a, 3b pushing away the soft tissue W laterally, in particular in the upper area of FIG. 2.

In addition in the present embodiment, all components are made of metal. In this case, a titanium alloy is used. The use of metallic materials makes possible a slim design of the blade elements and the base body. However, metallic blade elements may also be used in conjunction with a base body made of plastic. In this case, the plastic PEEK (polyether ether ketone) is particularly suitable as a matrix material in a composite material with carbon fibers or other fibers. A high-performance PEEK composite may be particularly advantageously used here with a carbon fiber proportion of up to 60%. Hardened or unhardened stainless steel and its alloys are another particularly suitable metallic material in addition to titanium and titanium alloys. The blade elements may be made first of a metallic material and then coated or recast with a plastic, whereby silicone is also particularly suitable for this in addition to the various forms of PEEK. By a coating or encapsulation of the metal cores of the blade elements with plastic, reflections may be reduced or avoided, allowing for better viewing of the operating area by the surgeon.

The double blade according to the invention is mounted to be freely rotatable in a corresponding seat on one arm of a suitable retractor. Identical double blades will usually be mounted on both arms of the retractor. After the surgeon has made an incision between two ribs of a patient, both double blades are inserted between two adjacent ribs. In this case, the surgeon is required to ensure the correct alignment of the base body, the double blades and the blade elements, so that the inner surfaces 3a4, 3b4 of the blade elements 3a, 3b abut the respective contact surfaces of the incision, while the bending of the distal ends 3a2, 3b2 engages with the ribs. Then, the retractor is expanded to allow the surgeon to view and access the surgery area. Since the ribs are not straight but are curved, the two blade elements 3a, 3b of a double blade twist so that their lateral direction is as parallel as possible to the respective contact surface. More specifically, each blade element 3a, 3b forms a tangent to a convex rib or contact surface and a secant to a concave contact surface or rib.

Figure 3:
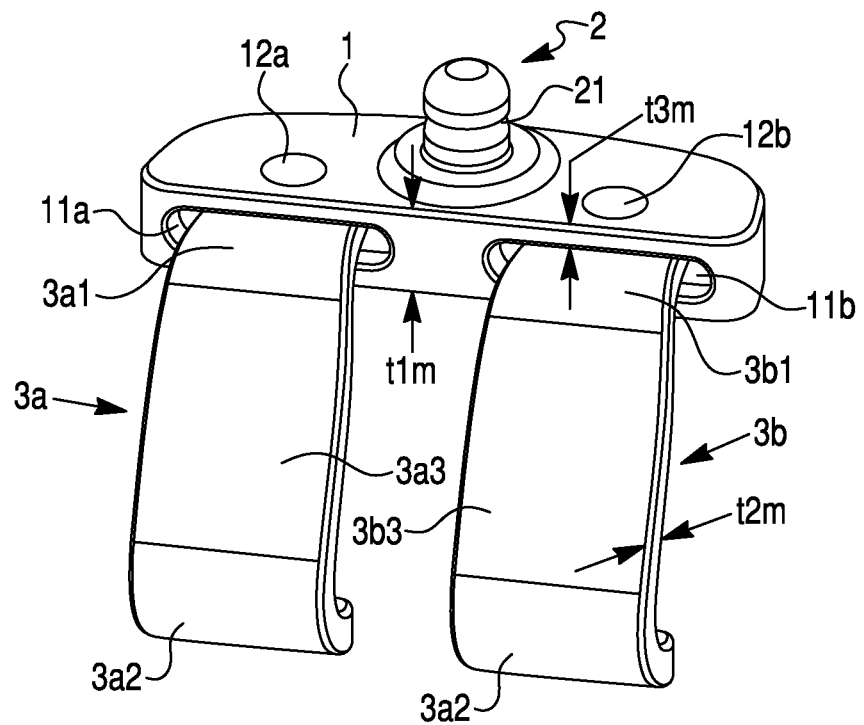
FIG. 3 shows a second embodiment of the present invention in a perspective view.
Figure 4:
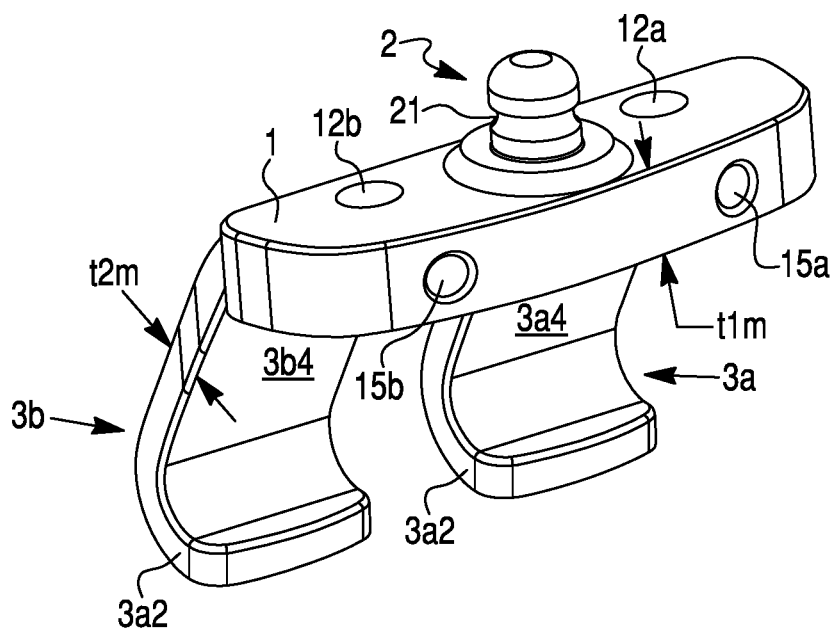
FIG. 4 shows a second embodiment of the present invention in a perspective view from the rear.

Hereinafter, a second embodiment of the present invention is described with reference to FIGS. 3 and 4.

The second embodiment has many similarities with the first exemplary embodiment. Therefore, the differences of the second embodiment with respect to the first embodiment are mainly described in the following.

The second embodiment is entirely made of plastic. In this case, PEEK (polyether ether ketone) is used. As PEEK, in contrast to titanium or a titanium alloy, has a lower strength, the components of the second embodiment are thicker than in the first embodiment. Thus, both the total thickness tm1 of the base body 1, the thickness t3m of the upper and lower walls of the base body 1 and the thickness t3m of the blade elements 3a, 3b of the first embodiment [sic] are, in each case, greater than the thickness tk1, tk2, tk3 of the corresponding component in the second embodiment. Even the mushroom-shaped mounting mandrel 2 has a more sturdy form due to its greater thickness. The slots 11a, 11b have a greater height to accommodate the thicker proximal ends 3a1, 3b1 of the two blade elements 3a, 3b. The two slots 11a, 11b also have a smaller width so that the rotatability of the blade elements 3a, 3b is more limited compared to the first embodiment. The web formed between the slots 11a, 11b is wider in order to provide the whole base body 2 with sufficient strength. In addition, the outer side walls of the two slots are again respectively arranged on the front side surface of the base body 2. This means that the slots 11a, 11b do not extend beyond the rounded corners of the base body 2 into the inside of the adjacent side surfaces.

Except for the thickness t2k of the blade elements 3a, 3b, their geometry is substantially identical to that of the blade elements of the first embodiment. Since the pins 12a, 12b with which the proximal ends 3a1, 3b1 of the blade elements 3a, 3b are rotatably mounted in the base body 2, are formed of plastic, they have a larger diameter as well. However, the greater thickness t2k of the blade elements 3a, 3b also means that dirt may easily accumulate in the slots 11a, 11b and be harder to remove. Therefore, as shown in FIG. 4, two cleaning openings 15a, 15b are provided on the rear side surfaces of the base body 1. Each of the cleaning openings 15a, 15b connects one of the slots 11a, 11b with the environment, and allows the introduction of a cleaning fluid to the respective proximal ends 3a1, 3a2 of the blade elements 3a, 3b, which are received in the slots 11a, 11b. It is particularly advantageous in this embodiment, that in each case a slot 11a, 11b and the associated cleaning opening 15a, 15b lie substantially in line so that a good flow of the cleaning fluid may be ensured without there being any areas where the flow might decrease sharply and thus not ensure the thorough cleaning of these areas. For a particularly easy and thorough cleaning, it is also advantageous if the distance between the inner wall of the slots 11a, 11b (i.e. the receiving seats) and the proximal ends 3a1, 3b1 of the respective blade elements 3a, 3b is not too narrow.

A connecting element is not shown in the figures. A connecting element is similar to a base body. At all the positions on a base body at which the pins 12a, 12b securing the blade elements 3a, 3b are provided, a mounting seat to receive a mounting mandrel 2 of a double blade is mounted on a connecting element. In addition, no blade elements are provided on a connecting element while the distance between the two mounting seats is greater than the distance between the two pins 12a, 12b in the case of a double-blade. A single blade is also not shown in the figures. This single blade has a shape corresponding to a blade element, but at its proximal end it features a mounting mandrel corresponding to the mounting mandrel 2 of the double blade in order to be received in a mounting seat of a connecting element and to be rotatably mounted. The length of the single blade may be greater than that of a blade element, so that the proximal bends of the single blade lie at essentially the same height as the blade elements of a double blade, so that a uniform engagement with the respective rib of the patient may be produced.

The present invention is described above with reference to use in the ribs of a patient, but it may also be used with other types of surgical retractors, for example, retractors used for the sternum of a patient.

Titanium, stainless steel, alloys of these two metals, different forms of PEEK and silicone are mentioned above as materials that may be used in the production of the double blades according to the invention. In principle, however, any metal may be used in the production of double blades according to the invention. The same is true for the plastics mentioned. Apart from the plastics mentioned, all plastics such as elastomers may be used. The various metals and plastics may be suitably and optionally combined in order to form the blade elements or the base body. In addition, the attachment of the blade elements to the base body may be ensured by means of various materials.

Other combinations of the individual features are possible and numerous other modifications and variations will become apparent to persons skilled in the art from the description and the appended claims and figures.

The invention claimed is:

1. A double blade for a surgical retractor comprising:
a base body comprising a top surface, a bottom surface opposite the top surface, and a front side surface extending between the top surface and the bottom surface;
a first slot formed in the front side surface, the first slot extending between a top wall and a bottom wall of the base body;
a second slot formed in the front side surface, the second slot extending between the top wall and the bottom wall of the base body;
and
a mounting mandrel extending from the top surface of the base body for rotatably mounting the base body to the surgical retractor,
the double blade having two and only two blade elements consisting of a first blade element mounted in the first slot and a second blade element mounted in the second slot,
the first blade element extending downwardly from the base body and freely rotatable in the first slot relative to the base body within a first range of rotation,
the second blade element extending downwardly from the base body and freely rotatable in the second slot relative to the base body within a second range of rotation,
the first blade element having a first central area that is planar, and the second blade element having a second central area that is planar,
the first blade element and second blade element being independently rotatable relative to the base body to automatically adapt to curved contact surfaces in an incision,
the first blade element and second blade element being independently rotatable relative to the base body to a first blade configuration in which the first central area forms a tangent to a first convex contact surface and the second central area forms a tangent to a second convex contact surface,
the first blade element and second blade element also being independently rotatable relative to the base body to a second configuration in which the first central area forms a secant to a first concave contact surface and the second central area forms a secant to a second concave contact surface.

2. The double blade according to claim 1, wherein the base body comprises a web extending between the top wall and the bottom wall, the web separating the first slot from the second slot.

3. The double blade according to claim 2, wherein the web limits the first range of rotation of the first blade element and limits the second range of rotation of the second blade element.

4. The double blade according to claim 2, wherein the web bisects the base body.

5. The double blade according to claim 1, wherein the first slot and the second slot each have an outer side wall.

6. The double blade according to claim 2, wherein the web is axially aligned with the mounting mandrel.

7. The double blade according to claim 1, wherein the mounting mandrel is configured to rotatably mount the double blade to a mounting seat of the surgical retractor.

8. The double blade according to claim 1, wherein the first blade element comprises a first proximal end and a first distal end, the first central area extending between the first proximal end and first distal end, and the second blade element comprises a second proximal end and a second distal end, the second central area extending between the second proximal end and the second distal end, the first and second proximal ends being rotatably mounted in the first and second slots respectively, and the first and second distal ends being free ends.

9. The double blade according to claim 8, wherein the first blade element comprises a first inner surface that faces the base body, and the second blade element comprises a second inner surface that faces the base body.

10. The double blade according to claim 9, wherein the first inner surface is flat in the first central area, and the second inner surface is flat in the second central area.

11. The double blade according to claim 8, wherein the first and second distal ends are bent toward the base body.

12. The double blade according to claim 8, wherein the first and second distal ends terminate in front of the front side surface of the base body.

13. The double blade according to claim 8, wherein the first central area is inclined relative to the first proximal end of the first blade element by a first acute angle, and the second central area is inclined relative to the second proximal end of the second blade element by a second acute angle.

14. The double blade according to claim 1, wherein the first range of rotation and the second range of rotation each comprise a range of inwards rotation, in which the first and second blade elements rotate toward one another, and a range of outwards rotation, in which the first and second blade elements rotate away from one another.

15. The double blade according to claim 14, wherein the range of outwards rotation is greater than the range of inwards rotation.

16. The double blade according to claim 1, further comprising a rear side surface opposite the front side surface.

17. The double blade according to claim 16, wherein the rear side surface defines at least one cleaning opening that connects with at least one of the first slot and the second slot.

18. The double blade according to claim 1, wherein the first blade element and second blade element are independently rotatable relative to the base body to a third configuration in which the first blade element and second blade element are co-planar to each other.

19. A double blade for a surgical retractor comprising:
a base body comprising a top surface, a bottom surface opposite the top surface, and a front side surface extending between the top surface and the bottom surface;
a first slot formed in the front side surface, the first slot extending between a top wall and a bottom wall of the base body;
a second slot formed in the front side surface, the second slot extending between the top wall and the bottom wall of the base body;
a first blade element rotatably mounted in the first slot by a first pin, the first blade element being rotatable within a first range of rotation relative to the base body;
a second blade element rotatably mounted in the second slot by a second pin, the second blade element being rotatable within a second range of rotation relative to the base body; and
a mounting mandrel extending from the top surface of the base body for rotatably mounting the base body to the surgical retractor,
the first blade element comprising a first proximal end mounted in the base body, a first central area attached to the first proximal end and extending out of the front side surface of the base body, and a first distal end attached to the first central area,
the first proximal end, first central area and first distal end forming a first one-piece monolithic body of unitary construction,
the second blade element comprising a second proximal end mounted in the base body, a second central area attached to the second proximal end extending out of the front side surface of the base body, and a second distal end attached to the second central area,
the second proximal end, second central area and second distal end forming a second one-piece monolithic body of unitary construction,
the first central area being inclined with respect to the first proximal end toward the bottom surface of the base body, the first central area forming a first acute angle with the first proximal end,
the second central area being inclined with respect to the second proximal end toward the bottom surface of the base body, the second central area forming a second acute angle with the second proximal end,
the first distal end and the second distal end being free ends,
the first central area and first distal end forming a first bend having a first obtuse angle, the first distal end bending toward the base body to form a first hook with the first central body, and
the second central area and second distal end forming a second bend having a second obtuse angle, the second distal end bending toward the base body to form a second hook with the second central body.

20. A double blade for a surgical retractor, the double blade comprising:
a base body having a top section and a bottom section that extends parallel to the top section,
the top and bottom sections of the base body defining a front side surface and a rear side surface opposite the front side surface,
the top and bottom sections separated by a first slot that extends in a plane between the top and bottom sections, the first slot extending partially through the base body and ending at a midsection between the front side surface and the rear side surface,
the top and bottom sections separated by a second slot that extends in a plane between the top and bottom sections, the second slot extending partially through the base body and ending at the midsection between the front side surface and the rear side surface,
a first blade element comprising a first proximal section mounted in the first slot, the first proximal section being planar and extending between the top and bottom sections,
a second blade element comprising a second proximal section mounted in the second slot, the second proximal section being planar and extending between the top and bottom sections,
the first proximal section being freely rotatable in the first slot relative to the base body within a first range of rotation,
the second proximal section being freely rotatable, independently of the first proximal section, in the second slot relative to the base body within a second range of rotation,
the first blade element having a first central section formed with the first proximal section as a first one-piece monolithic body, the first central section being inclined with respect to the first proximal section toward the bottom section of the base body,
the second blade element having a second central section formed with the second proximal section as a second one-piece monolithic body, the second central section being inclined with respect to the second proximal section toward the bottom section of the base body,
the first blade element and second blade element being independently rotatable relative to the base body to automatically adapt to curved contact surfaces in an incision.

* * * * *